US010881610B2

(12) United States Patent
Okushima et al.

(10) Patent No.: US 10,881,610 B2
(45) Date of Patent: Jan. 5, 2021

(54) ORALLY DISINTEGRATING TABLET

(71) Applicant: TOWA PHARMACEUTICAL CO., LTD., Kadoma (JP)

(72) Inventors: Tomoaki Okushima, Kadoma (JP); Keigo Nakamura, Kadoma (JP); Yutaka Okuda, Kadoma (JP)

(73) Assignee: TOWA PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/309,384

(22) PCT Filed: Jun. 15, 2017

(86) PCT No.: PCT/JP2017/022124
§ 371 (c)(1),
(2) Date: Dec. 12, 2018

(87) PCT Pub. No.: WO2017/217494
PCT Pub. Date: Dec. 21, 2017

(65) Prior Publication Data
US 2019/0125666 A1    May 2, 2019

(30) Foreign Application Priority Data
Jun. 16, 2016 (JP) ................. 2016-120015

(51) Int. Cl.
| A61K 9/00 | (2006.01) |
| A61K 47/02 | (2006.01) |
| A61K 47/26 | (2006.01) |
| A61K 47/32 | (2006.01) |
| A61K 47/36 | (2006.01) |
| A61K 47/38 | (2006.01) |
| A61K 9/20 | (2006.01) |
| A61K 31/551 | (2006.01) |

(52) U.S. Cl.
CPC ............. *A61K 9/0056* (2013.01); *A61K 9/20* (2013.01); *A61K 31/551* (2013.01); *A61K 47/02* (2013.01); *A61K 47/26* (2013.01); *A61K 47/32* (2013.01); *A61K 47/36* (2013.01); *A61K 47/38* (2013.01)

(58) Field of Classification Search
CPC .... A61K 9/0056; A61K 31/551; A61K 47/02; A61K 47/26; A61K 47/32; A61K 47/36; A61K 47/38; A61K 9/20
See application file for complete search history.

(56) References Cited

U.S. PATENT DOCUMENTS

| 7,749,533 | B2 * | 7/2010 | Fu ........................ | A61K 9/0056 424/464 |
| 2009/0117182 | A1 * | 5/2009 | Akutagawa .......... | A61K 9/0056 424/464 |
| 2014/0051733 | A1 * | 2/2014 | Beeram Reddy .... | A61K 9/2095 514/365 |

FOREIGN PATENT DOCUMENTS

| AU | 666666 | 2/1993 |
| AU | 699715 | 8/1995 |
| CA | 2629487 | 5/2007 |
| EP | 2133096 | 12/2009 |
| JP | S58-024410 | 2/1983 |
| JP | S58-024410 B | 5/1983 |
| JP | H06-502194 | 3/1994 |
| JP | 2004-315483 | 11/2004 |
| JP | 2006-022040 | 1/2006 |
| JP | 2009-515871 | 4/2009 |
| JP | 4446177 | 1/2010 |
| JP | 4551627 | 7/2010 |
| JP | 5062871 | 8/2012 |
| JP | 5062872 | 8/2012 |
| JP | 5584509 | 7/2014 |
| JP | 2015-78182 | 4/2015 |
| WO | 95/20380 | 8/1995 |
| WO | 2008/120548 | 10/2008 |
| WO | 2015/035114 | 3/2015 |
| WO | 2017/061426 A1 | 4/2017 |

OTHER PUBLICATIONS

International Search Report and Written Opinion, International Patent Application No. PCT/JP2017/022124, dated Sep. 12, 2017, with English translation of search report (12 pages).

* cited by examiner

*Primary Examiner* — Michael B. Pallay
(74) *Attorney, Agent, or Firm* — Hamre, Schumann, Mueller & Larson, P.C.

(57) ABSTRACT

An orally disintegrating tablet is disclosed possessing both advantageous hardness and disintegrability. The orally disintegrating tablet is (a) a compression molding product of a mixture comprising: a pharmaceutically active ingredient-containing composition selected from a group consisting of a pharmaceutically active ingredient-containing powder and pharmaceutically active ingredient-containing granules; rapidly disintegrating granules; and a lubricant, (b) wherein the rapidly disintegrating granules comprise a sugar and/or a sugar alcohol, and one or more organic and/or inorganic, hydrophilic and water-insoluble additives.

16 Claims, 1 Drawing Sheet

ORALLY DISINTEGRATING TABLET

TECHNICAL FIELD

The present invention relates to the field of tablet production, especially to the field of orally disintegrating tablet, and to an orally disintegrating tablet having sufficient hardness yet rapidly disintegrating in the presence of water.

BACKGROUND ART

An orally disintegrating tablet is a tablet that is designed so that the entire tablet disintegrates with saliva within a very short of time when put in the mouth, and has been developed as a form of tablet that can be easily taken by elders and infants (Patent documents 1-3).

An orally disintegrating tablet must have a property that it rapidly disintegrates when exposed to water (saliva) in the oral cavity. On the other hand, it must be able to keep the integrity of its initial form as a tablet without fracturing or wearing due to external forces like vibrations, physical shocks, or pressures in various foreseeable conditions of its handling in the course where it is produced in the form of tablet, packaged, shipped, transported in diverse circumstances, stored in medical facilities or pharmacies, pushed out of the package (blister pack) there and handed to a patient in a separate package, or pushed out of the blister pack by the patient just prior to use and put into the mouth. For this reason, it must have sufficiently high hardness so that it can withstand such external forces and escape fracturing or wearing. However, it is not easy to adequately realize both of those properties, easy disintegration and sufficient hardness, at the same time. This is because: although the more firmly are combined the components of the tablet such as a pharmaceutically active ingredient, excipients and other additives, the higher its hardness can become, which then very likely tends to render the tablet the less disintegrable; and conversely, while the weaker is the combination of those components, the higher its disintegrability becomes, which then leads to insufficient hardness and thus renders the tablet prone to fracturing and wearing on the way. Therefore, developmental activities have been conducted concerning how to provide an orally disintegrating tablet which possesses the both rather incompatible properties in good balance and also to improve the performance of orally disintegrating tablet, such as to find out a way to increase its disintegrability while achieving sufficiently high hardness (Patent documents 4-8).

On the other hand, the fast-paced aging of society is a factor that increases the need for the preparation form of orally disintegrating tablet. Thus, it is anticipated that orally disintegrating form of tablets will come to be demanded all the more frequently for conventional form of oral preparations widely used for various existing drugs. In order to be able to meet such a social demand, it is desirable that the form of orally disintegrating tablet can be surely utilized not only for some specific drugs but also other wide variety of ones, and further that orally disintegrating tablet with enhanced speed of disintegration can be provided.

PRIOR ART DOCUMENTS

Patent Documents

Patent document 1: JPS58-24410
Patent document 2: JPH06-502194
Patent document 3: WO95/20380
Patent document 4: JP4551627
Patent document 5: JP5584509
Patent document 6: JP5062761
Patent document 7: JP5062872
Patent document 8: JP4446177

SUMMARY OF INVENTION

Technical Problem

Against the above background, the present inventors fixed attention on the necessity of a means that enables, with drugs to be orally administered, easy formulation of orally disintegrating tablet having such advantageous properties as speedier disintegration when exposed to water, while having sufficiently high hardness.

Thus, it is an objective of the present invention to find out a universal means usable to formulate various orally administered drugs into the form of such an orally disintegrating tablet that is advantageous both in its hardness and disintegrability, and thereby to enable speedy provision of orally disintegrating tablets having such advantageous properties.

Solution to Problem

As a result of studies toward the above objective, the present inventors discovered certain granules (rapidly disintegrating granules) made of a composition falling within a certain range designed to give, by tableting, such a tablet that had sufficient hardness and very rapid disintegrability, and further found that an orally disintegrating tablets exhibiting both a sufficient hardness and remarkably improved disintegration speed at the same time, can be obtained by mixing the granules with a plain pharmaceutically active ingredient or its composition (a powder, or other granules as desired, referred also to pharmaceutically active ingredient-containing granules), and tableting the mixture in a conventional manner. The present invention was completed through further studies performed thereafter. Thus, the present invention provides what follows.

1. An orally disintegrating tablet that is
   (a) a compression molding product of a mixture comprising
   a pharmaceutically active ingredient-containing composition selected from a group consisting of a pharmaceutically active ingredient-containing powder and pharmaceutically active ingredient-containing granules; rapidly disintegrating granules; and a lubricant,
   (b) wherein the rapidly disintegrating granules comprise a sugar and/or a sugar alcohol, and one or more organic and/or inorganic, hydrophilic and water-insoluble additives.
2. The orally disintegrating tablet according to 1 above, wherein the pharmaceutically active ingredient-containing granules comprise a pharmaceutically active ingredient, an excipient, a disintegrant, and a binder.
3. The orally disintegrating tablet according to 1 or 2 above,
   wherein the organic, hydrophilic and water-insoluble additives are selected from the group consisting of starch, starch derivatives, cellulose derivatives, and crospovidone, and
   wherein the inorganic, hydrophilic and water-insoluble additives are selected from the group consisting of light anhydrous silicic acid, anhydrous calcium hydrogen phosphate, dried aluminum hydroxide gel, magnesium aluminosilicate, calcium silicate, magnesium silicate, synthetic aluminum silicate, hydrated silicon dioxide, calcium hydrogen phosphate, precipitated calcium carbonate, and magnesium aluminometasilicate.

4. The orally disintegrating tablet according to one of 1 to 3 above, wherein the proportion of the inorganic, hydrophilic and water-insoluble additives contained in the rapidly disintegrating granules is 0.3-5 weight %.

5. The orally disintegrating tablet according to one of 1 to 4 above, wherein the proportion of the organic, hydrophilic and water-insoluble additive contained in the rapidly disintegrating granules is 10-40 weight %.

6. The orally disintegrating tablet according to one of 1 to 5 above, wherein the proportion of the sugar and/or sugar alcohol contained in the rapidly disintegrating granules is 55-85 weight %.

7. The orally disintegrating tablet according to one of 1 to 6 above, wherein the rapidly disintegrating granules contain light anhydrous silicic acid as inorganic, hydrophilic and water-insoluble additives.

8. The orally disintegrating tablet according to one of 1 to 7 above, wherein the sugar and/or sugar alcohol is selected from the group consisting of mannitol and lactose.

9. The orally disintegrating tablet according to 8 above, wherein the rapidly disintegrating granules contain mannitol as the sugar and/or sugar alcohol, and a cellulose derivative, starch, and crospovidone as the organic, hydrophilic and water-insoluble additives.

10. The orally disintegrating tablet according to one of 1-9 above, wherein the mean particle size of the rapidly disintegrating granules is 10-300 μm.

11. The orally disintegrating tablet according to one of 1-10 above, wherein the proportion of the rapidly disintegrating granules in the total amount of the pharmaceutically active ingredient-containing granules and the rapidly disintegrating granules is 45-70 weight %.

12. The rapidly disintegrating granules according to one of 1-10 above.

13. A method for production of an orally disintegrating tablet comprising (a) a step of providing a pharmaceutically active ingredient-containing composition selected from a pharmaceutically active ingredient-containing powder and pharmaceutically active ingredient-containing granules, (b) a step of performing granulation to prepare rapidly disintegrating granules comprising spraying an aqueous suspension containing one or more organic, hydrophilic and water-insoluble additives to a fluid bed of a mixture containing inorganic, hydrophilic and water-insoluble additives, a sugar and/or a sugar alcohol, and organic, hydrophilic and water-insoluble additives, (c) a step of mixing the pharmaceutically active ingredient-containing composition and the rapidly disintegrating granules, adding at least a lubricant, and performing pressure molding.

14. The method for production according to 13 above, wherein the pharmaceutically active ingredient-containing granules comprise a pharmaceutically active ingredient, an excipient, a disintegrant, and a binder.

15. The method for production according to 13 or 14 above, wherein the organic, hydrophilic and water-insoluble additives are selected from the group consisting of starch, starch derivatives, cellulose derivatives, and crospovidone, and wherein the inorganic, hydrophilic and water-insoluble additives are selected from the group consisting of light anhydrous silicic acid, anhydrous calcium hydrogen phosphate, dried aluminum hydroxide gel, magnesium aluminosilicate, calcium silicate, magnesium silicate, synthetic aluminum silicate, hydrated silicon dioxide, calcium hydrogen phosphate, precipitated calcium carbonate, and magnesium aluminometasilicate.

16. The method for production according to one of 13 to 15 above, wherein the proportion of the inorganic, hydrophilic and water-insoluble additives contained in the rapidly disintegrating granules is 0.3-5 weight %.

17. The method for production according to one of 13 to 16 above, wherein the proportion of the organic, hydrophilic and water-insoluble additives contained in the rapidly disintegrating granules is 10-40 weight %.

18. The method for production according to one of 13 to 17 above, wherein the proportion of the sugar and/or sugar alcohol contained in the rapidly disintegrating granules is 55-85 weight %.

19. The method for production according to one of 13 to 18 above wherein the proportion of the rapidly disintegrating granules in the total amount of the pharmaceutically active ingredient-containing granules and the rapidly disintegrating granules is 45-70 weight %.

20. The method for production according to one of 13 to 19 above, wherein the inorganic, hydrophilic and water-insoluble additive is light anhydrous silicic acid.

21. The method for production according to one of 13 to 20 above, wherein the sugar and/or sugar alcohol is selected from mannitol, lactose, and trehalose.

22. The method for production according to one of 13 to 21 above, wherein the sugar and/or sugar alcohol is mannitol, and the organic, hydrophilic and water-insoluble additive in the mixture in step (b) is ethyl cellulose.

23. The method for production according to one of 13 to 22 above, wherein the additives in the aqueous suspension are starch and crospovidone.

24. The method for production according to one of 13 to 23 above, wherein the mean particle size of the rapidly disintegrating granules is adjusted to 10-300 μm.

Effects of Invention

The present invention according to one of the above definitions enables easy production of such an orally disintegration tablet, as compared before, that can, while having high hardness, bring about very rapid dispersion of the tablet's components in water, such as the pharmaceutically active ingredient-containing granules, independent from what the pharmaceutically active ingredient employed is or the composition including additives like excipients. Thus the present invention enables speedy, steady and easy production of orally disintegrating tablets advantageous both in its hardness and quick disintegration, for a wide variety of drugs.

DESCRIPTION OF EMBODIMENTS

Figure 1:
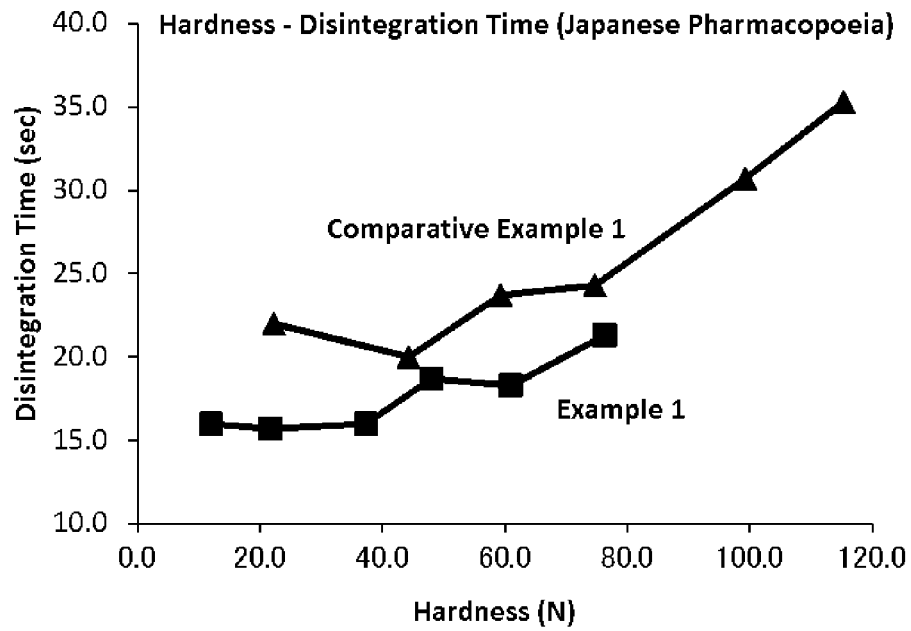
FIG. 1 is a graph illustrating the results of the Disintegration Test-1 (Japanese Pharmacopoeia) performed with the orally disintegrating tablets of Example 1 and Comparative Example 1 produced under different tableting pressures, in the relation between the hardness of the tablet (horizontal axis) and its disintegration time (vertical axis).

In the present invention, the phrase "pharmaceutically active ingredient-containing granules" means granules comprehensively that contain a medical drug for a disease to be treated or prevented. Herein, a "pharmaceutically active ingredient" may be chosen as desired in accordance with a given disease that is to be treated or prevented, and is not limited to a particular, specific medical drug. This is because the essence of the present invention resides in the structure and function of other granules (rapidly disintegrating granules) that are admixed before the tableting process conducted to immobilize the pharmaceutically active ingredient-containing granules into a tablet form.

In the present invention, the phrase "rapidly disintegrating granules" means such granules that possess a characteristic that they rapidly disintegrate in the presence of water even having been compressed into a tablet with sufficient hardness.

The present invention is characterized in preparing rapidly disintegrating granules that function in the presence of water to rapidly disperse materials comprising pharmaceutically active ingredient-containing granules, and in pressure molding the former granules along with the pharmaceutically active ingredient-containing granules into a tablet. An orally disintegrating tablet formed by pressure molding a mixture comprising the pharmaceutically active ingredient-containing granules and the rapidly disintegrating granules, is very rapidly disintegrated in its entirety (i.e., along with the pharmaceutically active ingredient-containing granules that are compressed into one body together with the intervening rapidly disintegrating granules) in the presence of water by the rapidly disintegrating granules compressed in the tablet. Thereby the function as orally disintegrating tablet fully works, and thus there is no particular limitation as to a specific pharmaceutically active ingredient to be employed in the pharmaceutically active ingredient-containing granules, or a composition of additives and the proportion of their content. Though not intended to be restricted by a theory, it is thought that in the present invention, due to the hydrophilic and water-insoluble additives contained as its components, each of the rapidly disintegrating granules rapidly sucks water in when exposed thereto and disposes water on its fine particle surfaces, and thereby a very thin layer of water is formed between any adjacent pair of components (such as each of rapidly disintegrating granules and pharmaceutically active ingredient-containing granules), which then cuts off the binding between the components simultaneously allowing further water to flow into the water layer from around the tablet, and rapidly destroys the consistency of the tablet (disintegrating the tablet) comprising pharmaceutically active ingredient-containing granules and rapidly disintegrating granules.

In the present invention, among the hydrophilic and water-insoluble additives as essential materials to form rapidly disintegrating granules, examples of preferred inorganic ones include light anhydrous silicic acid, anhydrous calcium hydrogen phosphate, dried aluminum hydroxide gel, magnesium aluminosilicate, calcium silicate, magnesium silicate, synthetic aluminum silicate, hydrated silicon dioxide, calcium hydrogen phosphate, precipitated calcium carbonate, and magnesium aluminometasilicate. Among these, particularly preferable examples include light anhydrous silicic acid, and anhydrous calcium hydrogen phosphate.

And examples of preferred organic, hydrophilic and water-insoluble additives include starch, starch derivatives, cellulose derivatives, and crospovidone. Examples of particularly preferred starch include corn starch and potato starch. Examples of particularly preferred starch derivatives include partly pregelatinized starch (PCS), and hydroxypropyl starch (HPS). Examples of preferred cellulose derivatives include, but not limited to, ethyl cellulose, hydroxypropyl cellulose, low substituted hydroxypropylcellulose, and hydroxypropylmethyl cellulose. Particularly preferred examples include ethyl cellulose.

Preferred examples of sugars and/or sugar alcohols, an essential component of rapidly disintegrating granules include, but not limited to, mannitol, lactose, and trehalose. Among these, mannitol is one of those particularly preferred.

In the case where rapidly disintegrating granules contain an inorganic, hydrophilic and water-insoluble additive (light anhydrous silicic acid, and the like), in order that the granules can, having been compressed by tableting into an immobilized state, accelerate speedy disintegration of the tablet in the presence of water, and also that the tablet has enough hardness in a dry state to escape impairment of its shape as a tablet by physical shocks or external forces it could receive during the course from its shipment up to its use, the proportion of inorganic, hydrophilic and water-insoluble additives contained in the rapidly disintegrating granules is preferably 0.3-5 weight %, more preferably 0.5-3 weight %, and particularly preferably 0.7-1.5 weight %.

In the case where rapidly disintegrating granules contain an organic, hydrophilic and water-insoluble additives (starch, ethyl cellulose, crospovidone, and the like), in order that the granules can, having been compressed by tableting into an immobilized state, accelerate speedy disintegration of the tablet in the presence of water, and also that the tablet has enough hardness in a dry state so as to escape impairment of its shape as a tablet during the course from its shipment up to its use, the proportion of organic, hydrophilic and water-insoluble additives is preferably 10-40 weight %, more preferably 15-35 weight %, and particularly preferably 18-32 weight %.

Rapidly disintegrating granules may contain as hydrophilic and water-insoluble additives, both of organic and inorganic ingredients, or only one of them, of which it is more preferable that both additives are contained at the same time. In the case where both are contained, the proportion of inorganic hydrophilic and water-insoluble additives contained in the rapidly disintegrating granules is preferably 0.3-5 weight %, more preferably 0.5-3 weight %, and particularly preferably 0.7-1.5 weight %, and the proportion of organic, hydrophilic and water-insoluble additives contained is preferably 10-40 weight %, more preferably 15-35 weight %, and particularly preferably 18-32 weight %.

Sugars and/or sugar alcohols contained in rapidly disintegrating granules act advantageously in driving further amount of water around the tablet into the interior of the rapidly disintegrating granules through the hydrophilic and water-insoluble additives, by creating localized high osmotic pressures upon coming into contact with a tiny amount of water and dissolving in it. The proportion of sugars and/or sugar alcohols contained in the rapidly disintegrating granules is preferably 55-85 weight %, more preferably 60-80 weight %, and particularly preferably 65-75 weight %.

In order that the rapidly disintegrating granules, an essential component of the orally disintegrating tablet of the present invention, rapidly disintegrate the tablet in the presence of water and disperse the pharmaceutically active ingredient-containing granules, the proportion of the rapidly disintegrating granules in the total amount of the pharmaceutically active ingredient-containing granules and the rapidly disintegrating granules, is preferably not less than 45 weight %, more preferable not less than 50 weight %, and particularly preferably not less than 55 weight %. Furthermore, in order that the tablet keeps hardness at required levels, the proportion is preferably not more than 70 weight %, and more preferably not more than 65 weight %, and most preferably not more than 60 weight %.

In the present invention, it is preferable that the particle size of rapidly disintegrating granules is not very large so that they can easily surround the pharmaceutically active ingredient-containing granules sufficiently. Thus, the mean particle size of the rapidly disintegrating granules is preferably 10-300 μm, more preferably 20-100 μm. Herein, "mean particle diameter" means the diameter ($D_{50}$) at which the accumulated amount of the particles reach 50% counted from the side of smaller particles in the particle distribution determined on laser diffraction scattering particle size distribution analyzer.

A preferred example of rapidly disintegrating granules is one that is produced by combining mannitol as sugars and/or sugar alcohols; light anhydrous silicic acid as inorganic hydrophilic and water-insoluble additives; and ethyl cellulose, starch and crospovidone as organic, hydrophilic and water-insoluble additives.

Production of the orally disintegrating tablet of the present invention can be carried out as described below.

1. Provision of Pharmaceutically Active Ingredient-Containing Granules.

In the present invention, pharmaceutically active ingredient-containing granules may be provided by granulation in a conventional manner using a proper amount of a pharmaceutically active ingredient of interest, and proper amount of a desired excipient, disintegrant, binder, and the like in a conventional manner 2. Rapidly Disintegrating Granules In the present invention, rapidly disintegrating granules may be made in the following manner, for example.

To a fluid bed of a mixture of an inorganic, hydrophilic and water-insoluble additive (e.g., light anhydrous silicic acid), a sugar and/or sugar alcohol (e.g., mannitol) and an organic, hydrophilic and water-insoluble additive (e.g., ethyl cellulose), is sprayed with an aqueous suspension of one or more organic, hydrophilic and water-insoluble additives (e.g., starch and crospovidone), dried and granulated. As desired, their particle distribution parameters, such as mean particle size, may be adjusted to a certain proper range by sizing. The proportion of each ingredient employed may be adjusted as desired so as to attain the proportion of ingredients, as described above for rapidly disintegrating granules.

3. Tableting

In a conventional manner, to pharmaceutically active ingredient-containing granules and rapidly disintegrating granules are added a small amount of lubricant, fluidizer, and the like, mixed well, and the mixture is tableted. The respective amount of pharmaceutically active ingredient-containing granules and rapidly disintegrating granules is adjusted so that the proportion of the rapidly disintegrating granules in the total amount of both granules represents preferably 45-65%, more preferably 60-80 weight %, and particularly preferably 65-75 weight %, and mixture of both granules is combined, if desired, with conventional additives that may be used for tableting such as lubricant and the like, mixed, and tableted to give orally disintegrating tablets having high hardness yet possessing remarkably increased disintegrability.

Besides, in the present invention, "hardness" is a value measured in accordance with the method described in Examples below. Namely, it is the measurement of the load (N) at the time when the tablet is broken by gradually pressed from is lateral sides with a jig of a hardness tester (TBH 425, ERWEKA).

Though there is no particular limitations as to the hardness of orally disintegrating tablet of the present invention, it is preferably not less than 55 N, more preferably not less than 60 N, still more preferably not less than 70 N, and particularly preferably not less than 90 N. However, hardness may be adjusted as desired in accordance with expected environment in which a given orally disintegrating tablet will be handled until use.

Further, the disintegration time-1 (Japanese Pharmacopoeia) of the orally disintegrating tablet of the present invention is preferably not more than 25 sec, more preferably not more than 22 sec, still more preferably not more than 20 sec, and particularly preferably 18 sec or less.

In the case where the disintegration time-2 is measured using OD-mate described in Examples below, it is preferably not more than 20 sec, more preferably not more than 15 sec, and further preferably not more than 10 sec.

EXAMPLES

While the present invention is described in further details with reference to examples, it is not intended that the present invention be limited to the examples.

(Example 1, Comparative Example 1) Orally Disintegrating Tablets

Orally disintegrating tablets of Example 1 and Comparative Example 1 were produced following the procedures mentioned later using each material at a proportion so as to give the tablets of the compositions shown in the table below.

TABLE 1

Orally Disintegrating Tablet

| | | | (Composition/Tablet) | |
| --- | --- | --- | --- | --- |
| | | | Example 1 | Comparative Example 1 |
| Pharmaceutically active ingredient | | Olanzapine: 10 mg | 100% | 100% |
| Granules | Excipient | D-mannitol | 71% | 69.2% |
| | Excipient | Ethyl cellulose | 2% | 4% |
| | Excipient | Light anhydrous silicic acid | 1% | — |
| | Excipient | Corn starch | 20% | 24% |
| | Excipient | Crospovidone | 6% | 2.8% |
| | | Granules: 258 mg | 100% | 100% |
| Lubricant | | Magnesium stearate: 2 mg | 100% | 100% |
| | | Tablet weight: 270 mg | | |

(Production Procedure)

1. Example 1

D-mannitol, ethyl cellulose, and light anhydrous silicic acid were mixed, and this mixture was put in a fluid bed granulator and sprayed with an aqueous suspension of corn starch and crospovidone in water, granulated, dried, and sized to give granules in a conventional manner. The granules, the pharmaceutically active ingredient (powder) and magnesium stearate were mixed, and tablets with the diameter of 9 mm were produced under application of different tableting pressures of 4 kN to 14 kN.

2. Comparative Example 2

In the same manner as in Example 1, except that light anhydrous silicic acid was not employed and the amount of excipient was correspondingly modified faintly, tablets with the diameter of 9-mm were produced as in Example 1.
(Method for Evaluation)
The hardness (N), tablet thickness (mm), and disintegration time (sec) were measured and recorded with the orally disintegrating tablets of Example 1 and Comparative Example 1, respectively.

1. Measurement of Hardness

A hardness tester (TBH 425, ERWEKA) was used to measure the hardness. This apparatus was designed to convey a tablet to a jig, by which the tablet is squeezed on its lateral sides with a gradually increasing pressure to determine the load (N) at the time when the tablet is broken.

2. Disintegration Test-1 (Japanese Pharmacopoeia)

A disintegration testing apparatus (compliant with Japanese Pharmacopoeia) was employed. In a glass vessel was put 900 ml of water at 37° C., and a basket (net-bottomed) containing tablets was moved up and down in the water contained in the vessel to measure the time required for the tablets to completely disintegrate (disintegration time-1).

3. Disintegration Time-2 (OD-Mate)

An oral disintegration testing apparatus simulating disintegration of tablet in the oral cavity (OD-mate, Higuchi Inc.) was used. Ten-ml water at 37° C. was put in small beakers and each tablet of Example 1 or Comparative Example 1, pinched with a jig, was immersed in the water, and the time for the upper portion of the jig to penetrate the tablet was measured and recorded (disintegration time-2).
(Result of Evaluation)
The results of the evaluation are shown in Table 2.

TABLE 2

|  |  | 4 | 6 | 8 | 10 | 12 | 14 |
|---|---|---|---|---|---|---|---|
|  | Tableting pressure (kN) |  |  |  |  |  |  |
| Example 1 | Weight (mg) | 271.4 | 271.2 | 272.1 | 271.0 | 270.4 | 270.5 |
|  | Thickness (mm) | 4.59 | 4.40 | 4.26 | 4.14 | 4.07 | 4.02 |
|  | Hardness (N) | 12.0 | 21.7 | 37.3 | 48.0 | 61.0 | 76.3 |
|  | Disintegration time-1 (sec) | 16.0 | 15.7 | 16.0 | 18.7 | 18.3 | 21.3 |
|  | Disintegration time-2 (sec) | 5.1 | 5.7 | 6.3 | 7.0 | 7.4 | 8.7 |
| Comparative Example 1 | Weight (mg) | 270.5 | 270.4 | 269.8 | 269.7 | 269.7 | 270.2 |
|  | Thickness (mm) | 4.56 | 4.34 | 4.22 | 4.13 | 4.06 | 4.01 |
|  | Hardness (N) | 22.3 | 44.3 | 59.3 | 74.7 | 99.3 | 115.3 |
|  | Disintegration time-1 (sec) | 22.0 | 20.0 | 23.7 | 24.3 | 30.7 | 35.3 |
|  | Disintegration time-2 (sec) | 8.5 | 10.8 | 12.7 | 17.8 | 21.3 | 24.5 |

Figure 2:
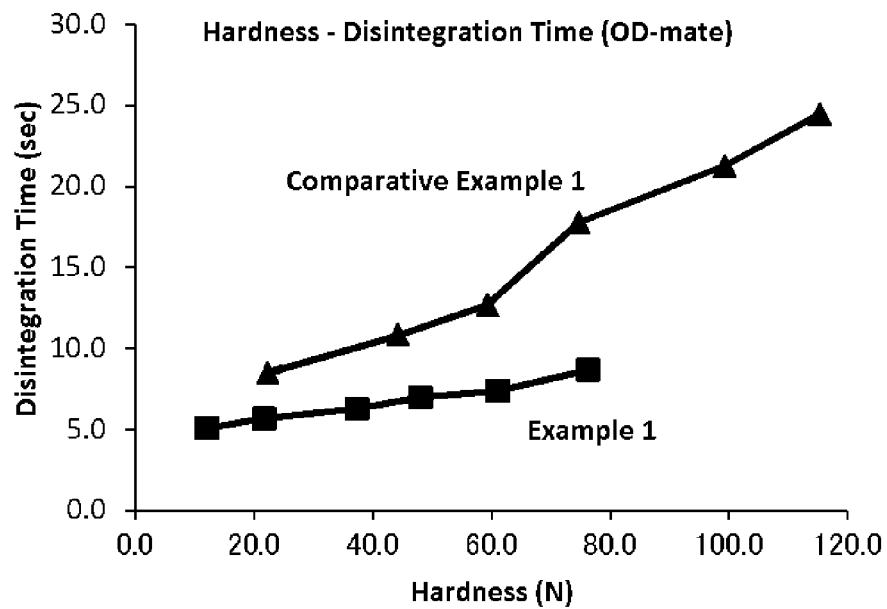
FIG. 2 is a graph illustrating the results of the Disintegration Time-2 conducted using OD-mate performed with the orally disintegrating tablets of Example 1 and Comparative Example 1 produced under different tableting pressures, in the relation between the hardness of the tablet (horizontal axis) and its disintegration time (vertical axis).

As seen in Table 2, the tablets of Example 1 exhibit much shorter time than those of Comparative Example 1 both in disintegration time-1 and disintegration time-2, as compared between tablets produced with the same tableting pressures. Further, as clearly discernible in FIGS. 1 and 2 that illustrate the relation between hardness and disintegration time-1 (Japanese Pharmacopoeia and OD-mate), the orally disintegrating tablets of Example 1, regardless their hardness, needs much shorter time for disintegration, than the orally disintegrating tablets of Comparative Example 1. The structural difference between Example 1 and Comparative Example 1 resides merely in the composition of their granules, indicating that it is the granules employed in Example 1 that remarkably improve the relation between the hardness and the rapid disintegrability of tablets.

(Example 2) Orally Disintegrating Tablet

Orally disintegrating tablets of Example 2 were produced following the procedures mentioned later using each material at a proportion so as to give the tablets of the composition shown in Table 3.

TABLE 3

Orally Disintegrating Tablet of Example 2

|  |  |  | (Composition/Tablet) |
|---|---|---|---|
| Pharmaceutically active ingredient-containing granules | Pharmaceutically active ingredient | Sildenafil Citrate | 50.3% |
|  | Excipients | D-mannitol, Carmellose calcium, Sodium carbonate, hydroxypropyl cellulose | 17.5% |
|  | Coating agent | Ethyl cellulose | 21.5% |
|  | Coating agent | Talc | 10.7% |
|  | Pharmaceutically active ingredient-containing granules: 279.2 mg |  | 100% |
| Rapidly disintegrating granules | Excipient | D-mannitol | 71% |
|  | Excipient | Ethyl cellulose | 2% |
|  | Excipient | Light anhydrous silicic acid | 1% |
|  | Excipient | Corn starch | 20% |
|  | Excipient | Crospovidone | 6% |
|  | Weight of quickly disintegrating granules: 345 mg |  | 100% |
| Added on Tableting | Disintegrant | Crospovidone | 62.1% |
|  | Sweetener | Aspartame | 25.1% |
|  | Flavor | Flavor | 1.1% |
|  | Fluidizer | Light anhydrous silicic acid | 2.5% |
|  | Lubricant | Magnesium stearate | 9.2% |
|  | Weight added on tableting: 56.4 mg Weight of tablet: 680.6 mg |  | 100% |

(Production Procedure)

1. Pharmaceutically Active Ingredient-Containing Granules

The pharmaceutically active ingredient and the excipients were granulated in a fluid bed granulator, dried, and sized to give granules in a conventional manner. The granules were coated with the coating materials consisting of ethyl cellulose and talc in a conventional manner to give pharmaceutically active ingredient-containing granules.

2. Rapidly Disintegrating Granules

D-mannitol, ethyl cellulose, and light anhydrous silicic acid were mixed, and this mixture was put in a fluid bed granulator, and sprayed with an aqueous suspension of corn starch and crospovidone to granulate, and dried to give rapidly disintegrating granules, in a conventional manner.

3. Mixing Ant Tableting

The pharmaceutically active ingredient-containing granules and the rapidly disintegrating granules were mixed with additives, and tableted into tablets with the diameter of 12-mm.

(Method for Evaluation)

The tablets thus obtained were measured for hardness, disintegration time-1 (Japanese Pharmacopoeia), disintegration time-2 (OD-mate) as in Example 1. The result was as follows.

(Result of Evaluation)

Hardness: 135 N
Disintegration time-1 (Japanese Pharmacopoeia): 17 sec
Disintegration time-2 (OD-mate): 8 sec As the result shows, the tablet of Example 2 exhibited remarkably rapid disintegrability compared with conventional orally disintegrating tablets, despite having high hardness.

(Example 3) Orally Disintegrating Tablet

Orally disintegrating tablets of Example 3 were produced following the procedures mentioned later using each material at a proportion so as to give the tablets of the composition shown in Table 4.

TABLE 4

Orally Disintegrating Tablet of Example 3

| | | | (Composition/Tablet) |
|---|---|---|---|
| Pharmaceutically active ingredient-containing granules | Pharmaceutically active ingredient | Sertraline hydrochloride | 46.7% |
| | Excipients | D-mannitol, Hydroxypropyl cellulose, Hypromellose, Talc | 15.8% |
| | Coating agent | Eudragit E | 30.0% |
| | Coating agent | Talc | 7.5% |
| | Weight of granules: 120 mg | | 100% |
| Rapidly disintegrating granules | Excipient | D-mannitol | 71% |
| | Excipient | Ethyl cellulose | 2% |
| | Excipient | Light anhydrous silicic acid | 1% |
| | Excipient | Corn starch | 20% |
| | Excipient | Crospovidone | 6% |
| | Weight of granules: 230 mg | | 100% |
| Added on tableting | Sweetener | Sucralose | 27.0% |
| | Colorant | Titanium dioxide | 34.7% |
| | Flavor | Flavor | 3.5% |
| | Fluidizer | Light anhydrous silicic acid | 8.7% |
| | Lubricant | Magnesium stearate | 26.1% |
| | Weight added on tableting: 10.36 mg | | 100% |
| | Weight of tablet: 360 mg | | |

(Production Procedure)

1. Employing the pharmaceutically active ingredient and the excipients, orally disintegrating tablets were produced in a fluid bed granulator, dried and sized to give granules in a conventional manner. The granules were coated with the coating materials in a conventional manner to give pharmaceutically active ingredient-containing granules.

2. Rapidly Disintegrating Granules

D-mannitol, ethyl cellulose, and light anhydrous silicic acid were mixed, and this mixture was put in a fluid bed granulator, sprayed with an suspension of corn starch and crospovidone in water to granulate, and dried to give rapidly disintegrating granules, in a conventional manner.

3. Mixing and Tableting

The pharmaceutically active ingredient-containing granules and rapidly disintegrating granules were mixed, and following further addition of excipients, mixed, tableted to produce tablets with the diameter of 10 mm.

(Method for Evaluation)

The tablets thus obtained were measured for hardness, disintegration time-1 (Japanese Pharmacopoeia) and disintegration time-2 (OD-mate) in the same manner as in Example 1. The result was as follows.

(Result of Evaluation)

Hardness: 90 N
Disintegration time-1 (Japanese Pharmacopoeia): 18 sec
Disintegration time-2 (OD-mate): 17 sec As shown in the above result, the tablet of Example 3 had a high hardness and exhibited remarkable disintegrability as compared with conventional orally disintegrating tablets.

INDUSTRIAL APPLICABILITY

The present invention is useful as it enables speedy, steady and easy production of orally disintegrating tablet that is advantageous both in its hardness and remarkably advantageous disintegrability in the presence of water, for a wide variety of medical drugs orally administered.

The invention claimed is:

1. An orally disintegrating tablet,
the tablet being a compression molding product of a mixture comprising:
a pharmaceutically active ingredient-containing composition selected from the group consisting of a pharmaceutically active ingredient-containing powder and pharmaceutically active ingredient-containing granules;
rapidly disintegrating granules; and
a lubricant,
wherein the rapidly disintegrating granules comprise:
a sugar alcohol;
organic hydrophilic and water-insoluble additives; and
an inorganic hydrophilic and water-insoluble additive,
wherein the organic hydrophilic and water-insoluble additives comprise starch or starch derivatives, crospovidone, and ethyl cellulose, and
the inorganic hydrophilic and water-insoluble additive is selected from light anhydrous silicic acid and magnesium aluminometasilicate, and
wherein the tablet has a hardness of not less than 60 N, and exhibits disintegration time of not more than 22 seconds as measured according to a Disintegration Test of Japanese Pharmacopoeia.

2. The orally disintegrating tablet according to claim 1, wherein the pharmaceutically active ingredient-containing granules comprise a pharmaceutically active ingredient, an excipient, a disintegrant, and a binder.

3. The orally disintegrating tablet according to claim 1, wherein the proportion of the inorganic hydrophilic and water-insoluble additive contained in the rapidly disintegrating granules is 0.3-5 weight %.

4. The orally disintegrating tablet according to claim 1, wherein the proportion of the organic hydrophilic and water-insoluble additives contained in the rapidly disintegrating granules is 10-40 weight %.

5. The orally disintegrating tablet according to claim 1, wherein the proportion of the sugar alcohol contained in the rapidly disintegrating granules is 55-85 weight %.

6. The orally disintegrating tablet according to claim 1, wherein the sugar alcohol is mannitol.

7. The orally disintegrating tablet according to claim 1, wherein the mean particle size of the rapidly disintegrating granules is 10-300 μm.

8. The orally disintegrating tablet according to claim 1, wherein the proportion of the rapidly disintegrating granules in the total amount of the pharmaceutically active ingredient-containing granules and the rapidly disintegrating granules is 45-70 weight %.

9. A method for production of an orally disintegrating tablet of claim 1, comprising:
providing a pharmaceutically active ingredient-containing composition selected from the group consisting of a pharmaceutically active ingredient-containing powder and pharmaceutically active ingredient-containing granules;
performing granulation to prepare rapidly disintegrating granules, comprising spraying an aqueous suspension comprising a first organic hydrophilic and water-insoluble additives to a fluid bed of a mixture comprising an inorganic hydrophilic and water-insoluble additive, a sugar alcohol, and a second organic hydrophilic and water-insoluble additives, wherein
the first and the second organic hydrophilic and water-insoluble additives respectively comprise starch or starch derivatives, crospovidone, and ethyl cellulose, and
the inorganic hydrophilic and water-insoluble additive is selected from light anhydrous silicic acid and magnesium aluminometasilicate; and
mixing the pharmaceutically active ingredient-containing composition and the rapidly disintegrating granules, adding at least a lubricant, and performing pressure molding.

10. The method for production according to claim 9, wherein the pharmaceutically active ingredient-containing granules comprise a pharmaceutically active ingredient, an excipient, a disintegrant, and a binder.

11. The method for production according to claim 9, wherein the proportion of the inorganic hydrophilic and water-insoluble additive contained in the rapidly disintegrating granules is 0.3-5 weight %.

12. The method for production according to claim 9, wherein the proportion of the organic hydrophilic and water-insoluble additives contained in the rapidly disintegrating granules is 10-40 weight %.

13. The method for production according to claim 9, wherein the proportion of the sugar alcohol contained in the rapidly disintegrating granules is 55-85 weight %.

14. The method for production according to claim 9, wherein the proportion of the rapidly disintegrating granules in the total amount of the pharmaceutically active ingredient-containing granules and the rapidly disintegrating granules is 45-70 weight %.

15. The method for production according to claim 9, wherein the sugar alcohol is mannitol.

16. The method for production according to claim 9, wherein the mean particle size of the rapidly disintegrating granules is adjusted to 10-300 μm.

\* \* \* \* \*